(12) United States Patent
Hong

(10) Patent No.: US 10,087,124 B2
(45) Date of Patent: Oct. 2, 2018

(54) PRODUCTION OF AROMATIC HYDROCARBONS

(71) Applicant: Oh Pharmaceutical Co. Ltd, Crown Point, IN (US)

(72) Inventor: Jin Ki Hong, Cypress, CA (US)

(73) Assignee: OH PHARMACEUTICALS CO. LTD, Crown Point, IN (US)

( * ) Notice: Subject to any disclaimer, the term of this patent is extended or adjusted under 35 U.S.C. 154(b) by 35 days.

(21) Appl. No.: 15/400,058

(22) Filed: Jan. 6, 2017

(65) Prior Publication Data

US 2018/0194701 A1    Jul. 12, 2018

(51) Int. Cl.
*C07C 2/46* (2006.01)
*B01J 8/24* (2006.01)
*B01J 8/18* (2006.01)

(52) U.S. Cl.
CPC .............. *C07C 2/46* (2013.01); *B01J 8/1836* (2013.01); *B01J 8/24* (2013.01); *B01J 2208/00132* (2013.01); *B01J 2208/00504* (2013.01); *C07C 2529/44* (2013.01)

(58) Field of Classification Search
CPC ....... C07C 2/76; C07C 15/00; C07C 2529/44; C07C 2529/67; C07C 2529/74; C10G 2300/1081; C10G 2400/30; C10G 45/70; B01J 2229/20; B01J 2229/42; B01J 29/068; B01J 29/44; B01J 29/67; B01J 29/7469; B01J 29/7492; B01J 37/0009; B01J 37/0201
See application file for complete search history.

(56) References Cited

U.S. PATENT DOCUMENTS

| | | | | |
|---|---|---|---|---|
| 9,873,647 | B2 * | 1/2018 | Iaccino | C07C 5/373 |
| 2009/0156870 | A1 * | 6/2009 | Lauritzen | C07C 2/66 585/24 |
| 2011/0196113 | A1 * | 8/2011 | Nesterenko | B01J 21/08 526/75 |
| 2013/0001064 | A1 * | 1/2013 | Lourenco | B01J 21/20 203/29 |

* cited by examiner

*Primary Examiner* — Sharon Pregler
(74) *Attorney, Agent, or Firm* — Lucas & Mercanti, LLP.

(57) ABSTRACT

A process for producing aromatic hydrocarbons from a light alkane feedstock such as an ethane-containing hydrocarbon stream is disclosed. The process comprises: contacting a light alkane feedstock comprising at least 50% ethane with a bi-functional aromatization catalyst in a fluidized bed reactor of bubbling or turbulent fluidization regime. The fluidized bed reactor comprise a catalyst bed, catalytic combustor and internal heat exchanger tubes embedded in the catalyst bed to provide the heat supply necessary for production of aromatic hydrocarbons. Continuous and uninterrupted production of aromatic hydrocarbons is realized by fluidly connecting multiple reactors in parallel and cycling operation of individual reactors between aromatics production mode and catalyst regeneration mode.

17 Claims, 7 Drawing Sheets

PRODUCTION OF AROMATIC HYDROCARBONS

FIELD OF THE INVENTION

The present invention relates to a process for producing aromatic hydrocarbons from a light alkane feedstock, such as an ethane or ethane containing hydrocarbon stream.

BACKGROUND OF THE INVENTION

Aromatic hydrocarbons such as benzene, toluene and xylene (collectively referred to in the industry as "BTX" or "light aromatics") play an important role in the chemical industry. For example, benzene is used to manufacture plastics, lubricants, rubbers, synthetic fibers and dyes. Toluene is used as a solvent for paint thinners, nail polish remover, glues, adhesives, rubber and disinfectants. Xylene is also used to produce plastics and synthetic fibers.

Aromatic hydrocarbons are derived from petroleum via various processes, such as catalytic reforming of naphtha or fluid catalytic cracking of heavy gas oil. Light alkanes can undergo a series of reactions when catalyzed by crystalline aluminosilicate and metals such as Pt, Ga, and/or Zn and produce industrially valuable aromatic hydrocarbons. Measurable quantities of methane, hydrogen, light alkanes, and light alkenes are also produced as by-products. Due to its plentiful presence and low cost driven by shale gas production, light alkanes provide opportunity for aromatic hydrocarbons production. However, there remain a number of technical obstacles for industrial scale production of aromatic hydrocarbons from light alkanes.

Light alkane aromatization is a strongly endothermic reaction, and therefore requires a large quantity of reaction heat supply at relatively high temperature. However, preheating the light alkane feedstock to provide sufficient sensible heat for the endothermic reaction is not feasible because the reaction heat required for industrially attractive rates is substantially larger than the quantity of sensible heat achievable through feedstock preheating. Excessive preheating of the feedstock in an attempt to increase its sensible heat and provide reaction heat may lead to a number of technical issues, including thermal breakdown of feedstock and shortened lifetime of preheating tubes. In addition, intensive heating-up of reactor tubes with small diameter in a furnace, which is conventionally used in steam methane reforming plants, would not be suitable for the light alkane conversion to aromatic hydrocarbons because its conversion rate is relatively low. Moreover, heating of reactor tubes packed with catalyst often creates undesirable temperature distribution in the catalyst bed, which leads to accelerated catalyst coking and sintering problems causing reversible or irreversible loss of catalyst activity. This imposes a burden on production cycle, equipment operation, system control, and overall process efficiency, and lowers aromatic hydrocarbons yield. A conventional way to regenerate deactivated catalyst is to burn off the coke with air or diluted air while aromatic hydrocarbons production process is stalled; hence, making it impossible to produce aromatic hydrocarbons in a continuous manner.

Taken together, there is a need for a new and improved process for producing aromatic hydrocarbons from light alkane feedstock by developing a uniform and reliable reaction heat supply to the catalyst bed and by making the entire process continuous.

SUMMARY OF THE INVENTION

To overcome the deficiencies of conventional process, a new and improved process for producing aromatic hydrocarbons from a light alkane feedstock is provided. The process of the present invention comprise the steps of feeding a light alkane feedstock comprising at least 50% ethane by weight into a fluidized bed reactor, wherein the reactor comprises a catalyst bed, a heat exchanger embedded in the catalyst bed and a catalytic combustor inside the heat exchanger. The feedstock contacts with the catalyst bed and drives bubbling or turbulent fluidization of catalyst particles at a temperature lower than 620° C. and at pressure between 0-200 psig to produce aromatic hydrocarbons. The catalyst bed comprises a bi-functional catalyst which comprises a dehydrogenation catalyst and a solid acid catalyst. Reaction by-products in the reactor effluent stream, such as methane and hydrogen, are separated from aromatic hydrocarbon products and sent to the catalytic combustor which produces hot flue gas that serves as heat source for the heat exchanger in the reactor. Unreacted light alkanes and other light hydrocarbon byproducts containing two to five carbons are recycled back to the reactor for further conversion.

Deactivated catalyst particles caused by coke buildup are regenerated by combustion of coke when feed conversion rate drops below the predetermined rate. Continuous and uninterrupted production of aromatic hydrocarbons from light alkane feedstock is realized by multiple reactor systems fluidly connected in parallel, wherein the individual reactors can undergo a transition between an aromatic hydrocarbons production mode and a catalyst regenerating mode in an orderly manner.

DETAILED DESCRIPTION OF THE INVENTION

Figure 1:
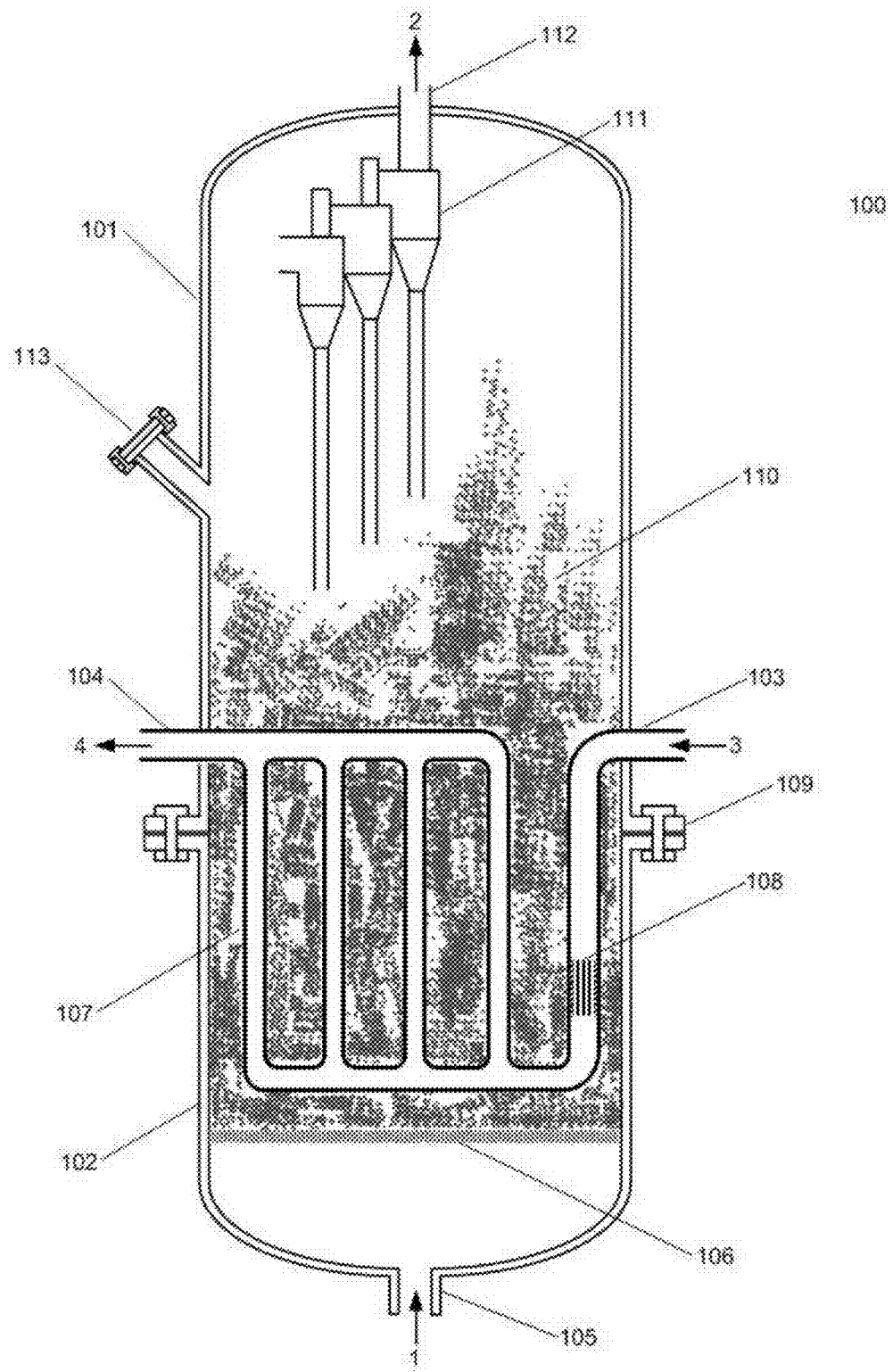
FIG. 1 illustrates an embodiment of a schematic process of the present invention for the production of aromatic hydrocarbons with a bubbling or turbulent flow fluidized bed reactor.

In order to solve the problems of conventional processes for producing aromatic hydrocarbons from light alkane feedstock such as ethane, the inventors have discovered a new and improved process for producing aromatic hydrocarbons that can be used with a single or a plurality of reactors with internal heat exchanger and internal catalytic combustor.

It should also be understood that singular forms such as "a," "an," and "the" are used throughout this application for convenience, however, except where context or an explicit statement indicates otherwise, the singular forms are intended to include the plural. Further, it should be understood that every journal article, patent, patent application, publication, and the like that is mentioned herein is hereby incorporated by reference in its entirety and for all purposes.

All numerical ranges should be understood to include each and every numerical point within the numerical range, and should be interpreted as reciting each and every numerical point individually. The endpoints of all ranges directed to the same component or property are inclusive, and intended to be independently combinable.

As used herein, the term "about" means within 10% of the reported numerical value, and preferably within 5% of the reported numerical value.

Before the present invention is described in detail below, it is to be understood that this invention is not limited to the particular methodology, protocols and reagents described herein, as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art.

Reaction

Catalytic conversion of light alkanes to produce aromatic hydrocarbons is initiated by contacting light alkanes with the dehydrogenation component of the bi-functional catalyst. In the presence of the bi-functional catalyst, light alkenes produced from the light alkane dehydrogenation undergo a series of reaction steps including oligomerization, cyclization, dehydrogenation, alkylation and cracking in a complex manner to produce aromatic hydrocarbons.

The catalytic conversion of light alkanes to aromatic hydrocarbons is strongly endothermic. At industrial level, this reaction requires a large quantity of heat supply to the catalyst bed to achieve commercially attractive aromatics production yield. The dehydrogenation step of the light alkane feed is mainly responsible for the reaction heat requirement.

Reaction heat supply to the catalyst bed is one of the major challenges in aromatic hydrocarbons production at industrial-scale. Uneven temperature distributions and hot spots in the catalyst bed shorten the cycle time between catalyst regeneration due to the accelerated coke build-up. Overheated catalyst also promotes unwanted heavy aromatics production and lowers the product quality. On the other hand, suboptimal low temperature of the catalyst bed or catalyst particles leads to reduced feed conversion rate. As such, supplying optimal amount of heat to the catalyst bed in a uniform manner is essential to achieve high product yield and quality.

Feedstock

The process can use any lower/light alkane or light paraffin feedstock including ethane, propane, butane or any combination of them. Feedstock for use with the present invention can be in the form of gas. Liquified feedstocks may also be used. Preferably, the lower or light alkane feedstock (or feedstock mixture) comprises at least 50% ethane, or 50-75% ethane, or 75-100% ethane. The percentages are expressed as weight percentages, but may also represent volume or mole percentages if so desired.

Catalysts

The process of the present invention utilizes a bi-functional catalyst. The bi-functional catalyst comprises an acid catalyst site provided by solid acid catalyst (e.g., zeolite) and a dehydrogenation catalyst site provided by noble (e.g., platinum, rhodium, palladium, etc.) or non-noble metals (e.g., iron, nickel, indium, gallium, etc.) or a noble metals-non-noble (attenuating) metals combination. More than one dehydrogenation catalysts may also be used, such as a Pt—Ga (platinum-gallium) or a Pd—Ga (palladium-gallium) combination. For example, both Pt and Ga or Pd and Ga can be co-impregnated into or co-loaded onto the zeolite or ZSM-5. The bi-functional catalyst may be of a size between 10-300 μm or between 30-300 μm in diameter.

In the preferred embodiment, the acid catalyst site is provided by zeolites. Zeolites are crystalline aluminosilicates which possess Bronsted acidic sites with ordered pore structure of molecular dimensions. For example, ZSM-5 has a medium size pore system consisting of straight channels (5.1 Å×5.5 Å) intersected by zigzag channels (5.3 Å×5.6 Å). The zeolite material used in the present invention may be selected from the group consisting of ZSM-5, ZSM-11, ZSM-12, ZSM-23, ZSM-35 and ZSM-48. Preferably, the surface area of the zeolite material used in the present invention is larger than 300 $m^2$ per gram. The zeolite material may be pretreated for conversion to $H^+$ form to impart sufficient acidity before introducing dehydrogenation component.

The dehydrogenation catalyst facilitates the dehydrogenation of ethane into ethylene, and the solid acid catalyst facilitates the oligomerization of ethylene to hexene followed by the cyclization of hexene into cyclohexane. Subsequently the bi-functional catalyst facilitates the conversion of cyclohexane to the desired aromatic hydrocarbon products. In addition, the two catalyst sites of the bi-functional catalyst may be adjacent to each other so that olefins (ethylene) formed as an intermediate (through dehydrogenation) can proceed to the next consecutive reaction until aromatic hydrocarbons are formed as a final product without being limited by mass transfer.

The bi-functional catalyst may optionally include binder material to better hold individual zeolite particles together to maintain overall catalyst particle size in the optimal range and provide physical strength or attrition resistance for fluidized reactor operation in bubbling or turbulent flow regime. The binder may be selected from the group consisting of alumina or silica or various clay materials and is added to metal-loaded zeolite powder. Binder content in the catalyst of this invention may be in the range of 10-50 wt % of the finished bi-functional catalyst (including the binder). Binder is mixed thoroughly with metal-loaded zeolite powder before being transferred to spray drying or other mechanical operation for particles formation. Preferably, the finished bi-functional catalyst particles (which include the binder) are 30-300 micrometers in size and spherical in shape.

Preferred bi-functional catalyst includes the following solid acid catalyst loaded with the following dehydrogenation catalyst. The dehydrogenation catalyst loading is calculated on metal basis as a wt % of the finished bi-functional catalyst which includes the binder.

ZSM-5 loaded with 0.02-0.2 wt % Pt
ZSM-5 loaded with 0.05-0.15 wt % Pt
ZSM-5 loaded with 0.04 wt % Pt
ZSM-5 loaded with 0.5-2.0 wt % Ga
ZSM-5 loaded with 1.0-2.0 wt % Ga In an exemplary embodiment, to prepare the bi-functional catalyst for use in the present invention, dehydrogenation catalyst components such as platinum and gallium are deposited in the form of salt solution. A commonly known method such as ion-exchange method, incipient wetness method or excessive water method is used to deposit the metals. After deposition of the metal, the zeolite powder is dried and calcined. Platinum is highly active in dehydrogenation of light alkanes. Platinum metal loading is preferably less than 0.2 wt % (such as 0.02-0.15 wt %) considering its prohibitively high material cost in industrial scale process and the utilization rate of platinum.

Gallium exhibits mild dehydrogenation activity for light alkane feed. Highly affordable and less volatile market price of gallium compared to platinum and its beneficial effect on feed dehydrogenation rate and product selectivity render gallium as one of the candidate for dehydrogenation element in bi-functional catalyst. It is preferred that gallium when combined with platinum can contribute to the light alkane feed conversion and aromatic hydrocarbon product selectivity. Preferably, the bi-functional catalyst comprises 0.02-0.2 wt % Pt and 0.5-2.0 wt % Ga loaded on ZSM-5.

Catalyst Regeneration

Due to coking and other activities resulting in the loss of catalytic activity, the bi-functional catalyst particles may be regenerated as part of the process of the present invention. The regeneration step includes burning off coke or other materials which contribute to the loss of catalytic activity.

In an exemplary embodiment of the present invention, bi-functional catalyst particles are regenerated when the feed conversion rate drops below a predetermined rate. The catalyst regeneration procedure includes (1) stop feeding light alkane feedstock, (2) purging the reactor with nitrogen to remove remaining light alkane and other hydrocarbon molecules, (3) replacing nitrogen with diluted air for coke burn-off, and (4) burning off the coke while maintaining fluidization of catalyst particles in bubbling or turbulent fluidization regime throughout the regeneration period at the reactor or catalyst bed temperature preferably of 400-600° C. and at the reactor pressure of 0-200 psig. When coke burn-off is completed, diluted air feeding should be stopped and the reactor is purged with nitrogen to remove remaining oxygen.

Reactor Process

Fluidization is the operation by which solid particles are transformed into a fluidlike state through suspension by a gas. When inlet gas is passed through the bottom plate at very low velocity, the particles remain in a fixed state. However, as the inlet velocity is increased to a critical velocity of inlet gas, called minimum fluidization velocity, the particles start to move apart and vibrate. A further increase of the inlet gas velocity leads to particles getting suspended by the upward flowing gas. With the increase in gas velocity, various regimes of fluidization are observed. Smooth fluidization progresses to bubbling fluidization and further to turbulent fluidization until particles are carried out of the bed with the gas.

Fluidized bed reactors (FBR) are heterogeneous catalytic reactors in which the mass of catalyst is fluidized. This allows for extensive mixing in all directions. The heat transfer rate in a fluidized bed reactor can be five to ten times greater than that in a packed-bed reactor. Moving particles, especially small particles, can transport heat much more efficiently than gas alone. Even for the most extreme exothermic reactions, a fluidized bed can maintain an isothermal profile within a few degrees. Another benefit of fluidized beds is the ability to move solids in a fluid-like fashion. Catalyst can be added or removed from the reactor without requiring a shutdown.

A fluidized bed reactor may contain a plenum, a fluidization plate, such as a grid plate or sparger, the catalytic bed region, a freeboard region above the catalytic bed, heating and cooling coils if needed, and cyclones. The primary purpose of the fluidization plate is to provide good gas distribution and drive fluidization of catalyst particles or catalyst bed. Fluidization plates can range from simple fine porous plates to bubble cap plates. Fine porous plates are made of sintered metal powder and its pore size is regulated. Bubble cap grid plates are designed to minimize particle weeping into the plenum and used in large scale fluidization process. Spargers can be designed with jets that point downward, upward, or laterally. Sparger designs can have ring, orthogonal, or treed layouts. Grids and sparger can be equipped with shrouds to minimize particle attrition and to better direct the gas.

In the present invention, as shown in FIG. 1, the fluidized bed reactor 100 results in both improved heat supply to the catalyst bed and uniform catalyst bed temperature through fast and violent movement of catalyst particles coupled with strong mixing. In an exemplary embodiment with a vertical fluidized bed reactor, the light alkane feed moves upward through the catalyst bed or catalyst particles at a gas velocity greater than dense bed transition velocity, but less than transport velocity for the catalyst particles. As the flow rate is regulated for bubbling or turbulent fluidization regime, entrainment of particles by the gas flow is limited. Cyclone separators can be used to separate these catalyst particles from the exiting reactor effluent stream 2 and return these particles to the catalyst bed.

In an exemplary embodiment, a plurality of cyclones can be installed in the upper vessel 101 of the reactor 100. In this multiple cyclone arrangement, the gas outlet of the first cyclone is channeled directly to the inlet of the second cyclone, and so on. This use of multiple cyclones improves the overall separation efficiency and keeps the overall catalyst losses to a minimum.

Driven by fluid-like behavior of catalyst particles, heat transfer coefficients, as high as several hundred $W/m^2$-K is readily achievable compared to sub-100 $W/m^2$-K in non-fluidized heat transfer cases. The high thermal mass of catalyst particles impinging heat exchanger tube surface with high frequency substantially improves heat supply.

Uniform catalyst bed temperature is attributable to large surface area of catalyst particles circulating inside the reactor in a chaotic manner and in contact with surrounding gas stream. When leaving the bed, the gas temperature is close to the catalyst particle temperature. The temperature difference between different points in the catalyst bed is less than 2-5° C. This is a significant improvement from highly non-uniform temperature distribution found in industrial-scale fixed bed or circulating fluidized bed reactors for hydrocarbon conversion. Heat supply through the fixed catalyst bed is highly limited as the catalyst in the stationary position itself impedes heat transfer. As a result, steep temperature gradient develops along or across the fixed catalyst bed. In circulating fluidized bed reactors, on the other hand, a wide variation of temperature in catalyst particles over a short cycle is continuously repeated. Catalyst particles experience repeated cycles of heating-up to over 700° C. during catalyst regeneration and cooling-down to below 550° C. during cracking reaction. Circulating fluidized bed reactor, which relies mainly on coke burn-off and hot regenerated catalyst circulation for reaction heat supply, is not suitable for light alkane conversion because coke yield in light alkane conversion is insufficient to meet the reaction heat supply for the industrially attractive conversion rate. Compared to 5 mole % or higher coke yield generally obtainable in catalytic cracking of gas oil using circulating fluidization system, light alkane conversion to aromatic hydrocarbons produces coke yield which is lower than 1 mole %. This low coke yield can not provide enough reaction heat through coke burn-off for industrially attractive conversion rate in a circulating fluidization system. Further, the hardware system for circulating fluidized bed reactor is not suitable for introduction of external heat source to meet the required reaction heat supply.

FIG. 1 shows a schematic of the process of the present invention using a fluidized bed reactor. The reactor 100 comprises a lower vessel 102 and an upper vessel 101. The lower vessel 102 includes a reactor inlet 105 for the reactor feed stream 1, fluidization plate 106 and bed of catalyst particles 110. The upper vessel 101 can include single or a plurality of internal cyclone separators 111, a reactor outlet 112 for the reactor effluent stream 2, a service port 113 for catalyst loading or inspection window, heat exchanger 107 and catalytic combustor 108. Upper vessel 101 is mounted vertically on top of the lower vessel 102 with flange connection 109. The flange connection makes it easier to access various components inside the reactor for inspection and maintenance during non-operation and also provides gas tight sealing between the upper vessel 101 and lower vessel 102 during operation.

Bed of catalyst particles 110 is loaded above the fluidization plate 106 in the lower vessel 102. Embedded inside the bed of catalyst particles 110 are the heat exchanger 107 and the catalytic combustor 108. Located inside heat exchanger 107, the catalytic combustor 108 receives fuel gas-air mixed stream 3 through the catalytic combustor inlet 103 which is mounted to the upper vessel 101. After entering the catalytic combustor inlet 103, the fuel gas-air mixed stream 3 is heated by the hot fluidized catalyst particles and gas stream inside the reactor before reaching the catalytic combustor 108. At the end of the heat exchanger 107 is a heat exchanger outlet 104 for the heat exchanger effluent 4 to exit. The heat exchanger 107 may be in the form of heat exchanger tubes.

The catalytic combustor 108 initiates and maintains combustion of fuel gas-air mixed stream 3, which is a mixture of air and fuel gas comprising methane and hydrogen, to release thermal energy. The catalytic combustor 108 uses combustion catalyst supported or coated over ceramic or metallic substrate with honeycomb or porous foam structure. Either platinum group metals such as palladium, platinum or rhodium or metal oxides such as chromium oxide or perovskites are used as combustion catalyst. Compared to conventional combustor, catalytic combustor operates over wide range of air-fuel ratios and produces reduced NOx emission. Also, the low light-off temperature achievable (for example, below 300° C. or even below 200° C.) for catalytic combustor reduces reactor start-up time. Catalytic combustor 108 mounted inside the heat exchanger 107 offers advantage over the combustor external to the reactor. With an external combustor, combustion of fuel-air mixture occurs outside the reactor and the hot combustion effluent produced flows through insulated pipe and enters heat exchanger inside the reactor to serve as heat source. The transfer of hot combustion effluent from the external combustor to the heat exchanger in the reactor creates high level of thermal stress in the connecting areas of reactor and effluent transfer pipe and accelerates mechanical failure. The catalytic combustor 108 of the present invention produces hot combustion effluent (i.e., heat exchanger effluent 4) inside the reactor and subsequently transfers the effluent to the heat exchanger which is also internal to the reactor. The hot combustion effluent stream produced serves as heat source for reaction heat supply through the heat exchanger 107. Heat exchanger effluent 4, after losing its thermal energy, leaves through the heat exchanger outlet 104. There is no direct contact of the hot combustion effluent with the reactor vessel and, therefore, the issue of thermal stress associated with the hot combustion effluent can be avoided. Additionally, the issue of heat loss associated with the hot combustion effluent transfer and insulation of the transfer line to minimize heat loss can be retired.

Reactor feed stream 1 enters the lower vessel 102 through reactor inlet 105 and flows upward through fluidization plate 106. The fluidization plate is in the form of either fine porous metal plate/disk, bubble cap plates or spargers for fluidization of catalyst particles. Gas flow rate is regulated in order to achieve either bubbling or turbulent fluidization of catalyst particles in the reactor. Flow regime lower than dense bed transition velocity or higher than transport velocity is not desirable for the present invention. Combustion of fuel gas-air mixed stream 3 occurs through the catalytic combustor 108 and the stream temperature is raised above 700° C. The hot effluent stream from the catalytic combustor 108 flows through the heat exchanger 107 and serves as heat source for the reaction heat supply. Preferably, catalyst bed temperature is maintained at 520-620° C. range during aromatic hydrocarbons production mode operation and 400-600° C. during catalyst regeneration mode operation. Before leaving the reactor 100, the product gas stream goes through cyclone(s) 111 and fine catalyst particles are separated from the reactor effluent stream 2 and returned to the catalyst bed 110.

Preferred temperature ranges less than 620° C. for the process of the present invention include between 400-620° C., 500-600° C., 500-620° C., between 450-550° C., between 550-620° C., between 540-590° C. or about 550° C. Such relatively lower range of working temperature compared to that of conventional process enables increased temperature gradient between the heat source inside the heat exchanger and catalyst bed. The relatively low reaction temperature increases heat transfer rate by augmenting temperature gradient or, more specifically, logarithmic mean temperature difference (LMTD) between the heat source flowing through the embedded heat exchanger tube and catalyst bed. Further, catalyst bed temperature above 620° C. is not desirable from aromatic hydrocarbons product yield perspective. At temperatures above 620° C., the enhanced conversion rate of light alkane feed driven by elevated temperature drops rapidly by the accelerated coke build-up in the catalyst particles. This leads to shortened production time before catalyst regeneration and reduced aromatic hydrocarbons production yield.

The reaction heat for conversion of ethane to aromatics (benzene formation for example) is 343 kJ/mole of benzene. At 1000 barrel-per-day aromatics production scale, the reactor requires roughly 6-7 megawatt of heat transfer rate to the catalyst bed in order to meet the reaction heat requirement at the target production rate—an energy requirement that can be achieved by using the embedded heat exchangers in the fluidized bed process of the present invention.

The reactor pressure is determined based on a number of process design elements that include reaction kinetics, fluidization behavior, process units sizing, auxiliary power requirements and separation efficiency. The preferred pressure range is between 0-200 psig, such as 20-200 psig, 40-200 psig, or 60-200 psig.

Single Reactor Process with Recycling

In another exemplary embodiment, the process of the present invention may include both a reactor process for producing aromatic hydrocarbons and a separation process for separating aromatic hydrocarbons in the reactor effluent stream. A vapor-liquid separator generally referred to as a flash drum, knock-out drum or knock-out pot can be used to separate a vapor-liquid mixture in the separation process. The separation process may also include unconverted light alkanes separation from fuel gas. Unconverted light alkanes are recycled back to the reactor process for conversion into aromatic hydrocarbons. Fuel gas, comprising methane and hydrogen, serves as heat source for the light alkanes conversion in the reactor.

Figure 2:
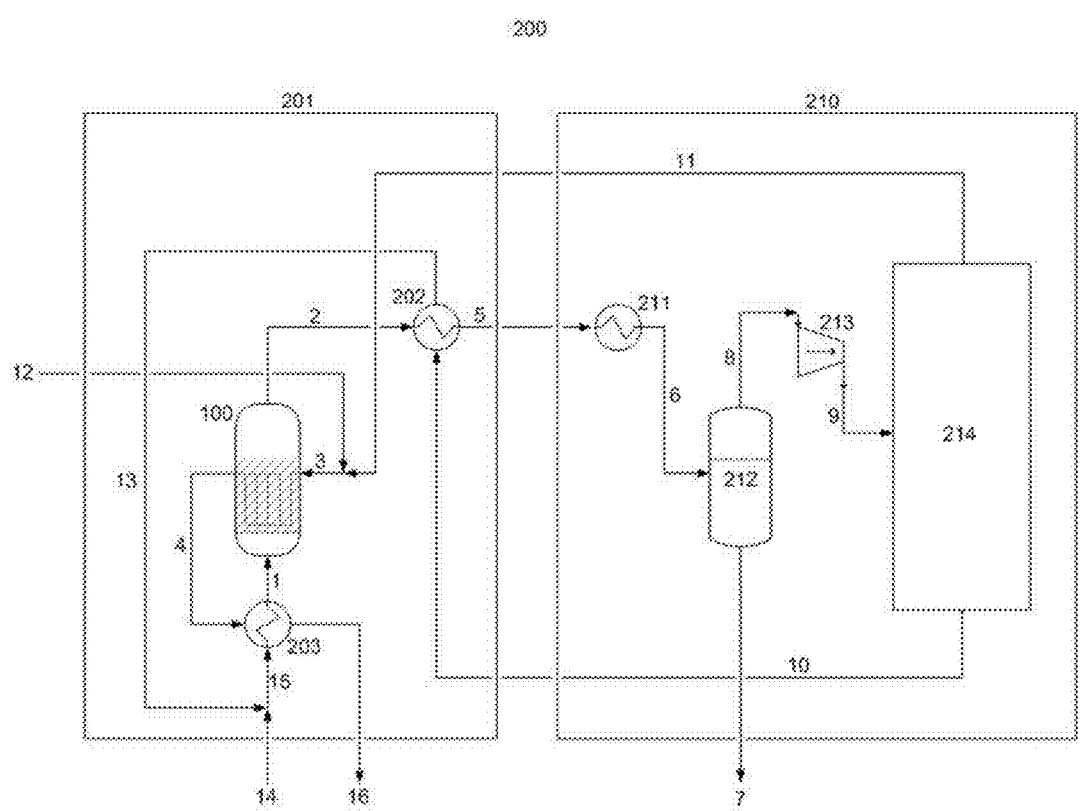
FIG. 2 illustrates another embodiment of a schematic process of the present invention for the production of aromatic hydrocarbons with a single fluidized bed reactor.

For example, FIG. 2 shows a single reactor process 200 that comprises reactor sub-process 201 and separation sub-process 210. Light alkane fresh feed 14 may be optionally mixed with light alkane recycle stream 13 and may optionally enter a heat exchanger 203 for preheating before entering the reactor 100. The reactor feed stream 1, with or without further preheating, enters fluidized bed reactor 100. The process of producing aromatic hydrocarbons can then proceed, for example, as already shown and discussed above for FIG. 1. The catalyst bed temperature is maintained at the desired temperature range, which can be 520° C.-620° C. or another temperature range as discussed above.

Reactor effluent stream 2 may be subsequently cooled below 300° C. in a heat exchanger (cooler) 202 before entering the separation sub-process 210. The cooled reactor effluent stream 5 from a heat exchanger 202 enters another heat exchanger 211 in order to drop the reactor effluent stream temperature below 20° C. and subsequently enters a vapor-liquid separator 212 wherein the liquid product 7, which is mainly aromatic hydrocarbons, is separated from the gaseous product stream 8.

The gaseous product stream 8 from the separator 212 is then directed to a compressor 213 and its pressure is elevated to 200 psig or higher before entering demethanizer 214. The demethanizer 214 serves to further separate the gaseous product stream 9 into a light alkane recycle stream 10 and a fuel gas stream 11. The light alkane recycle stream 10, which comprises unreacted ethane and other hydrocarbons containing two to five carbons, is recycled back to the reactor sub-process 201 and combined with light alkane fresh feed 14 before entering reactor 100 for conversion into aromatic hydrocarbons. Recycling of the light alkane recycle stream 10 enables the conversion of the light alkane feed into completion.

Figure 3:
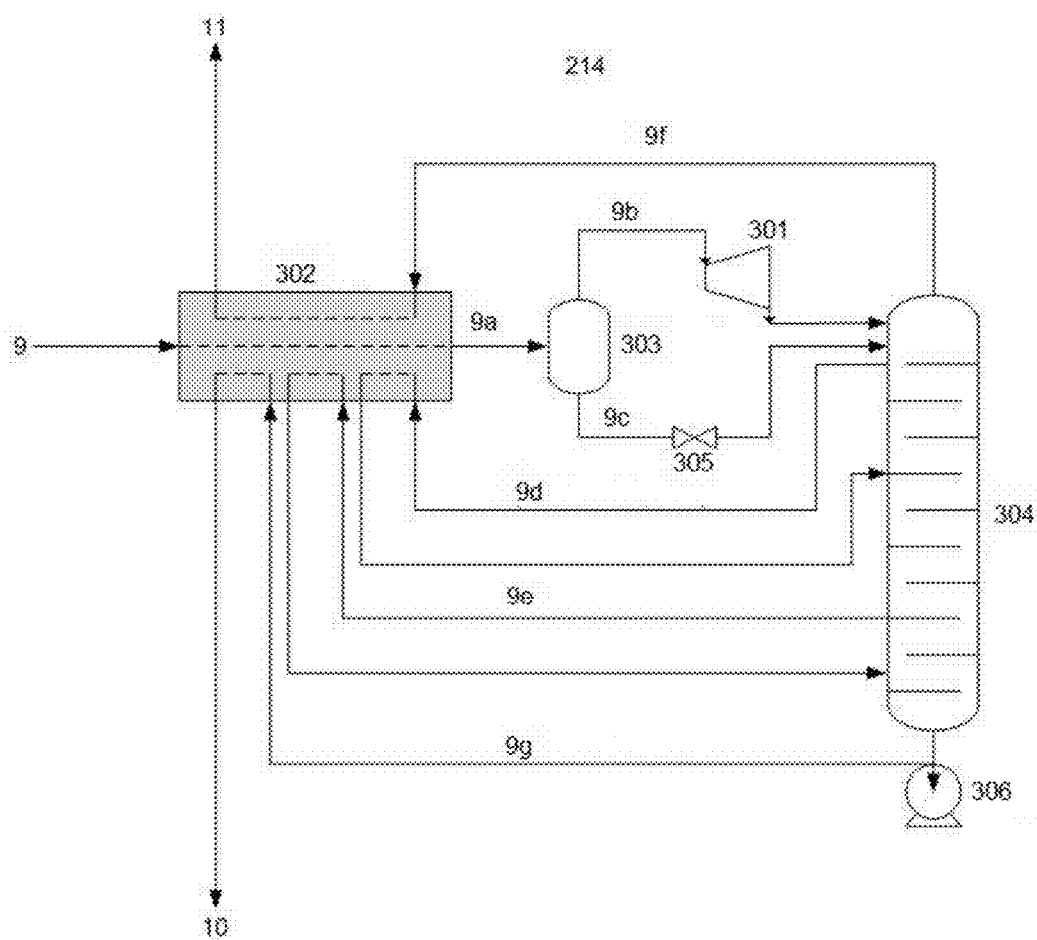
FIG. 3 illustrates the schematic process of a demethanizer.

Demethanizer 214 is a low-temperature process and is used to separate natural gas liquids such as ethane, propane and butane from methane. As schematically shown in FIG. 3, demethanizer 214 includes turboexpander 301, cold box 302 (an array of heat exchangers integrated), gas-liquid separator 303 and demethanizer fractionation column 304. The gaseous product stream 9 entering the demethanizer 214 is first cooled to about −30° C. or below in a cold box 302 which partially condenses the gaseous product stream 9. The resultant gas-liquid mixture 9a is then separated into a gas stream 9b and a liquid stream 9c. The liquid stream 9c from the gas-liquid separator flows through a valve 305 and undergoes a throttling expansion that results in lowering the temperature of the stream to about −40° C. or below as the stream enters the demethanizer fractionation column 304. The gas stream from the gas-liquid separator enters a turboexpander 301 where it undergoes isentropic expansion and the expansion lowers the gas stream temperature to about −55° C. or below as it enters the column. Liquid stream 9d from the top tray of the column is routed through the cold box 302 where it is warmed as it cools the gaseous product stream 9, and is then returned to the lower section of the column. Another liquid stream 9e from the lower section of the column is routed through the cold box and returned to the column. The overhead gas product stream 9f from the column is routed through the cold box 302 where it is warmed as it cools the gaseous product stream 9 before leaving the demethanizer as the fuel gas stream 11. The bottom product stream 9g (which can be pumped using pump 306 to cold box 302) from the column is also warmed in the cold box 302 before leaving the demethanizer as the light alkane recycle stream 10. The configuration of the demethanizer as shown in FIG. 3 and the operation conditions as specified above should not be construed as limited but can be modified in various ways to meet specific objectives under various process conditions.

As shown in FIG. 2, the fuel gas stream 11 is directed to the reactor sub-process 201 and mixed with the combustion air 12 to form fuel gas-air mixed stream 3 before entering the catalytic combustor inlet 103 in the reactor 100 to undergo combustion as it passes through the catalytic combustor 108 (as shown in FIG. 1) and form heat exchanger effluent 4 (i.e., the hot flue gas) which serves as heat source for the reaction while flowing through the heat exchanger 107.

After the heat exchanger effluent 4 exits the fluidized bed reactor 100, the remaining sensible heat of the heat exchanger effluent 4 can be further utilized in a heat exchanger 203 for the optional preheating of the reactor feed stream 15.

In production mode of a reactor sub-process, the fluidized bed reactor is operated preferably with feed WHSV (weight hourly space velocity, the ratio of hourly feed supply rate compared to catalyst weight) of 0.5-5.0/hour, catalyst particles or bed temperature of 520-620° C., and reactor pressure of 0-200 psig. In regeneration mode, the reactor is operated preferably with catalyst particles or catalyst bed temperature of preferably 400-600° C. and reactor pressure of 0-200 psig.

Multiple Reactor Process

In yet another exemplary embodiment, the process of the present invention may include multiple reactors instead of a single reactor for producing aromatic hydrocarbons. Furthermore, similar to FIG. 2, there may also be a separation process to separate unconverted light alkanes for recycling back to the reactor process. The separation process may also include separating fuel gas to provide a source for producing hot flue gas that will heat one or more reactors for the aromatic hydrocarbons production.

Figure 4:
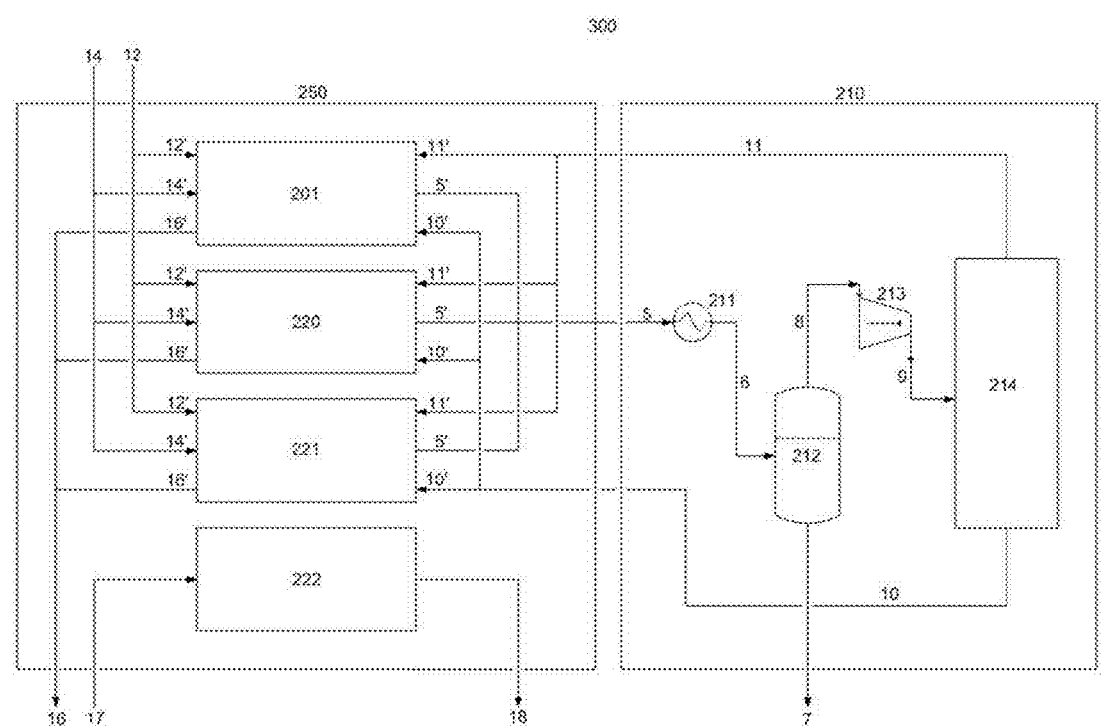
FIG. 4 illustrates yet another embodiment of a process of the present invention for the production of aromatic hydrocarbons with multiple fluidized bed reactors.

In an exemplary embodiment such as shown in FIG. 4, the multiple reactor process 300 of the present invention may include multiple reactor sub-process 250 and a separation sub-process 210.

As shown in FIG. 4, the multiple reactor sub-process 250 may include multiple reactor sub-processes e.g., 201, 220, 221, and 222 aligned in parallel. Each reactor sub-process may be similar to the reactor sub-process for producing aromatic hydrocarbons as described above for FIG. 2. Multiple reactors can work continuously in such a way that one reactor sub-process is in regeneration mode for coke burn-off, while the other reactor sub-processes are in production mode. The duration of production mode operation may take between 12 hours and 96 hours.

In FIG. 4, light alkane fresh feed 14 is split into individual light alkane fresh feed 14'. The individual light alkane fresh feed 14' are supplied to the individual reactor sub-processes 201, 220, and 221 in production mode. The reactor effluent streams 5' from individual reactor sub-processes 201, 220, and 221 may be combined and the combined reactor effluent stream 5 subsequently goes through another heat exchanger 211 of the separation sub-process 210. Similar to what was described for FIG. 2, the combined reactor effluent stream 5 is cooled below 20° C. after going through the heat exchanger 211 and is directed to the vapor-liquid separator 212 in order to separate the liquid product 7 from the gaseous product stream 8. The gaseous product stream 8 goes through a compressor 213 and the stream pressure is elevated to above 200 psig. The pressurized gaseous product stream 9 undergoes extremely low temperature separation (−55° C. or below) in the demethanizer 214.

Fuel gas stream 11 comprising mainly methane and hydrogen leaves the demethanizer 214 and is split into individual fuel gas streams 11' before entering individual reactor sub-processes in production mode. The air stream 12 is split into individual air streams 12' before entering the individual reactor sub-processes. The individual air stream 12' is then mixed with the individual fuel gas stream 11'. The mixed fuel-air stream then enters the catalytic combustor inlets of individual fluidized bed reactors and subsequently undergoes combustion reaction through the catalytic combustor as shown in FIG. 1. The hot flue gas generated from the catalytic combustor flows through the heat exchanger and serves as heat source for the reaction heat needed for the aromatic hydrocarbons production from light alkane.

Uncoverted ethane and other hydrocarbons containing two to five carbons are separated in the demethanizer 214 into a light alkane recycle stream 10, which is then further split into individual light alkane recycle streams 10' before entering individual reactor sub-processes 201, 220 and 221 in production mode. The individual light alkane fresh feeds 14' are combined with the individual light alkane recycle streams 10' in the reactor sub-process and the combined stream enters the reactor for aromatic hydrocarbons production.

As shown in FIG. 4, there may be a single reactor sub-process 222 which is in regeneration mode (as opposed to production mode). Reactor sub-process 222 in regeneration mode remains fluidly disconnected from the reactor sub-processes in production mode and separation sub-process, which means that the light alkane fresh feed 14, air 12, light alkane recycle stream 10 and fuel gas stream 11 do not enter the reactor sub-process in regeneration mode. Instead, diluted air 17 is supplied to the reactor through reactor inlet 105 in the reactor sub-process 222 in regeneration mode while catalyst bed temperature is maintained at 400-600° C. range. Monitoring of $CO_2$ concentration in the catalyst regeneration effluent stream 18 provides information on the progress of coke burn-off and readiness of the reactor sub-process for transition into production mode.

As byproduct of light alkane aromatization, coke continues to build up within the catalyst particles over the course of aromatization reaction. Coke build-up leads to a gradual drop in alkane feed conversion and shift in product selectivity. The conventional scheduled burn-off of coke with air or diluted air requires alternation between production and catalyst regeneration mode. Shifting between the two different modes upsets reactor effluent stream and its downstream separation system operations. However, present invention uses an integrated process which enables continuous production of aromatic hydrocarbons and minimizes interference in separation system operation.

When feed conversion rate of a reactor drops below the predetermined rate, the reactor is fluidly disconnected from the separation sub-process and the other aromatic hydrocarbons production reactors before performing the catalyst regeneration procedure described above.

When the catalyst regeneration procedure is completed, the reactor is fluidly reconnected to the separation sub-process and other reactors in production mode for aromatic hydrocarbons production.

Continuous and uninterrupted production of aromatic hydrocarbons from light alkane feedstock is realized by multiple reactor sub-processes fluidly connected in parallel, wherein the individual reactors can undergo a transition between an aromatic hydrocarbons production mode and a catalyst regeneration mode in an orderly manner.

EXAMPLES

Having thus described the basic concept of the invention, it will be rather apparent to those skilled in the art that the foregoing detailed disclosure is intended to be presented by way of example only, and is not limiting. Various alterations, improvements, combinations and modifications will occur and are intended to those skilled in the art, though not expressly stated herein. These alterations, improvements, combinations and modifications are intended to be suggested hereby, and are within the spirit and scope of the invention.

Example 1

Catalyst samples with the following metal loadings were prepared.
  Catalyst A: 0.04 wt % Pt/ZSM-5/Binder
  Catalyst B: 0.04 wt % Pt-1.2 wt % Ga/ZSM-5/Binder
  Catalyst C: 0.04 wt % Pt-1.6 wt % Ga/ZSM-5/Binder
Loadings are weight percentage of metals (Pt and/or Ga in metallic form) in the finished catalyst.

Catalyst A, B and C were prepared on ZSM-5 zeolite powder. CBV3024E ZSM-5 powder, available from Zeolyst and 30:1 molar ratio of $SiO_2/Al_2O_3$, was calcined at 550° C. for 5 hours in order to convert to $H^+$ form from ammonium form. 50 gram samples of the above ZSM-5 powder was mixed with 100 mL of deionized water and the slurry was vigorously stirred. Appropriate amount of diluted salt solutions of tetraamine platinum chloride for Pt source and gallium nitrate for Ga source were mixed. The mixed salt solution was added dropwise to the ZSM-5 slurry under vigorous stirring. The slurry was held at 75° C. for 24 hours under vigorous stirring and in a refluxing set-up. The zeolite slurry was then dried gradually over 6 hour period. The metal catalyst loaded ZSM-5 powder was further dried at 120° C. for 2 hours, raised to 650° C. and held for 2 hours for calcination.

Appropriate amount of binder material, Sasol DISPERAL® P2, was added to 100 mL deionized water and the mixture was vigorously stirred for homogeneous emulsion. The amount of binder material was determined for 4:1 weight ratio of metal catalyst loaded ZSM-5 vs binder material and this translates to 20 wt % binder material. The metal catalyst loaded ZSM-5 powder after sintering was added to the emulsion. The emulsion was slowly heated for water evaporation under vigorous stirring. When the water content was low enough through evaporation of the deionized water and the remaining paste of binder and metal catalyst loaded ZSM-5 mixture became thick enough, then manual extrusion was performed to obtain catalyst extrudate. The diameter of the dried catalyst extrudate was in the range of 1.9-2.1 mm. The extrudate was calcined at 650° C. The calcined extrudate was ground and sieved for catalyst particles with 106-180 micrometer range particle size. The catalyst particles thus prepared is called finished catalyst.

10.0 gram of the finished catalyst particles was loaded in a fluidized bed reactor made of quartz. Quartz frit served as fluidization plate. The reactor diameter was 22 mm and the catalyst bed height in stationary state was approximately 45 mm. The reactor was sitting in the center of a split tube furnace and had enough space for feed preheating. Two thermocouples installed 10 mm below and 20 mm above the fluidization plate, respectively, provided feed preheating temperature and catalyst bed temperature.

After catalyst loading into the reactor, the reactor was fed with nitrogen flowing upwardly. The reactor temperature was raised over 2 hour period under nitrogen flow. Once the target furnace temperature was reached, ethane flow corresponding to the weight hourly space velocity (WHSV) of 1.0/hour was introduced. Nitrogen flow was adjusted so that ethane/nitrogen molar flow rate into the reactor was 3/1 ratio. Nitrogen served as internal reference for quantitative analysis of hydrocarbons products using gas chromatography. The reactor pressure was maintained at ambient pressure and no pressurization of the reactor was attempted. A liquid knock-out unit was installed downstream of the reactor for collection of liquid products. The knock-out unit was cooled to −5° C. using a circulating chiller. After introducing ethane and nitrogen, the feed was maintained for 24 hours. During the 24 hour run period, the feed preheating temperature and catalyst bed temperature were stable at 540° C. and 560° C., respectively. Gaseous product stream, after leaving the knock-out unit, was split and part of the stream was sent to an online gas chromatography. Based on composition data obtained from the gas chromatography analysis, ethane conversion and other hydrocarbon product selectivities up to C4s were computed according to the following formulas.

$$\%=100\times(1-(C_2H_6/N_2)_{RE}/(C_2H_6/N_2)_{FEED}) \quad \text{Ethane Conversion,}$$

%=100×(moles of carbon in hydrocarbon product $i$ in reactor effluent/moles of carbon in reacted ethane)  Selectivity of Hydrocarbon Product i, where $(C_2H_6/N_2)_{RE}$ is ethane to nitrogen molar ratio in the reactor effluent and $(C_2H_6/N_2)_{FEED}$ is ethane to nitrogen molar ratio in the feed stream, respectively.

Gas chromatography analysis was performed every hour over the 24 hour run period. Liquid product collected in the knock-out units over the 24 hour run period was taken out after the 24 hour run period has reached and its composition was determined using a detailed hydrocarbon analyzer. Selectivity toward coke was determined from the amount of $CO_2$ produced during catalyst regeneration step.

Figure 5:
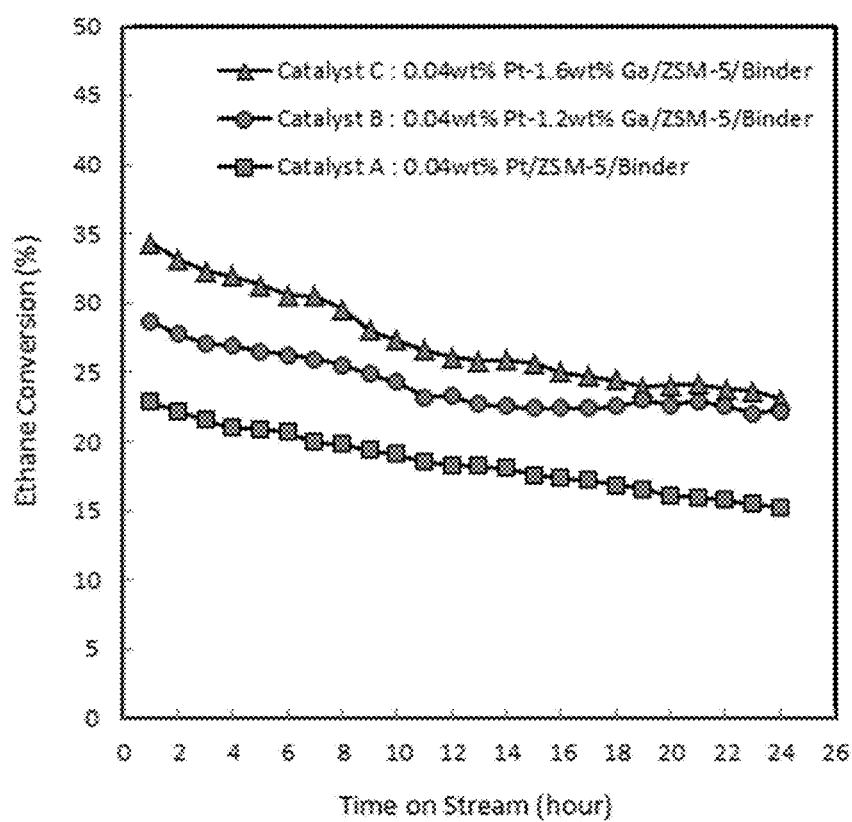
FIG. 5 shows the ethane feed conversion over a 24 hour run period in a fluidized bed reactor for the three catalyst compositions as described in Example 1.

FIG. 5 shows ethane conversion with time on stream (24 hour run period) for the three catalyst compositions. Ethane conversion gradually dropped with time on stream, mainly driven by coke build-up in the catalyst.

Figure 6:
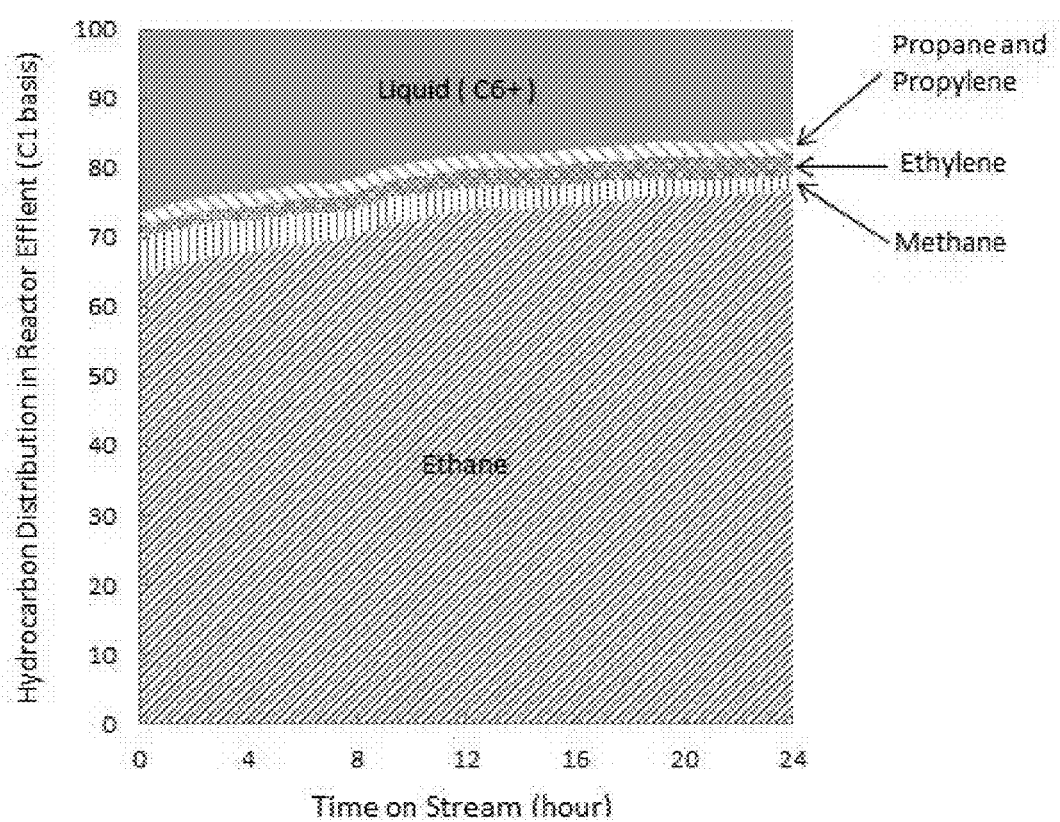
FIG. 6 shows the hydrocarbon distribution (carbon molar basis) in the reactor effluent over a 24 hour run period for Catalyst C (0.04 wt % Pt-1.6 wt % Ga/ZSM-5/Binder) in a fluidized bed reactor as described in Example 1.

FIG. 6 shows the hydrocarbon distribution measured over the 24 hour run period in the reactor effluent stream for Catalyst C (0.04 wt % Pt-1.6 wt % Ga/ZSM-5/Binder). As time on stream progressed, ethane conversion dropped gradually and there was change in individual product selectivities.

Table 1 compares the aromatization reaction performance averaged over the 24 hour run period for the three catalysts. The data in Table 1 indicate that addition of Ga to Pt in the bi-functional catalyst increased both ethane conversion and product selectivity toward aromatic hydrocarbon liquids (C6+).

TABLE 1

|  | Catalyst | | |
| --- | --- | --- | --- |
|  | A | B | C |
| Pt Loading, wt % | 0.04 | 0.04 | 0.04 |
| Ga Loading, wt % | 0.0 | 1.2 | 1.6 |
| Ethane Conversion | 18.5 | 24.2 | 27.3 |
| Selectivities, % (carbon basis) | | | |
| Methane | 14.0 | 9.4 | 11.8 |
| Ethylene | 18.7 | 12.9 | 10.4 |
| Propane | 5.3 | 6.0 | 5.3 |
| Propylene | 4.8 | 2.9 | 2.3 |
| Liquid (C6+) | 56.7 | 67.3 | 68.6 |
| Coke | 0.5 | 1.4 | 1.6 |

Example 2

Catalyst C (0.04 wt % Pt-1.6 wt % Ga/ZSM-5/Binder) was run for 24 hour period for aromatic hydrocarbons production from ethane feed and subsequently was regenerated by diluted air. For regeneration, 60 SCCM of air diluted with 120 SCCM nitrogen flow was fed to the catalyst bed upwardly. Furnace temperature was raised from 400° C. to 600° C. over 4 hour period and gas chromatography analysis of the regeneration effluent stream was performed every 15 minutes for measurement of $CO_2$ production rate, which is used for coke yield or coke selectivity determination.

Figure 7:
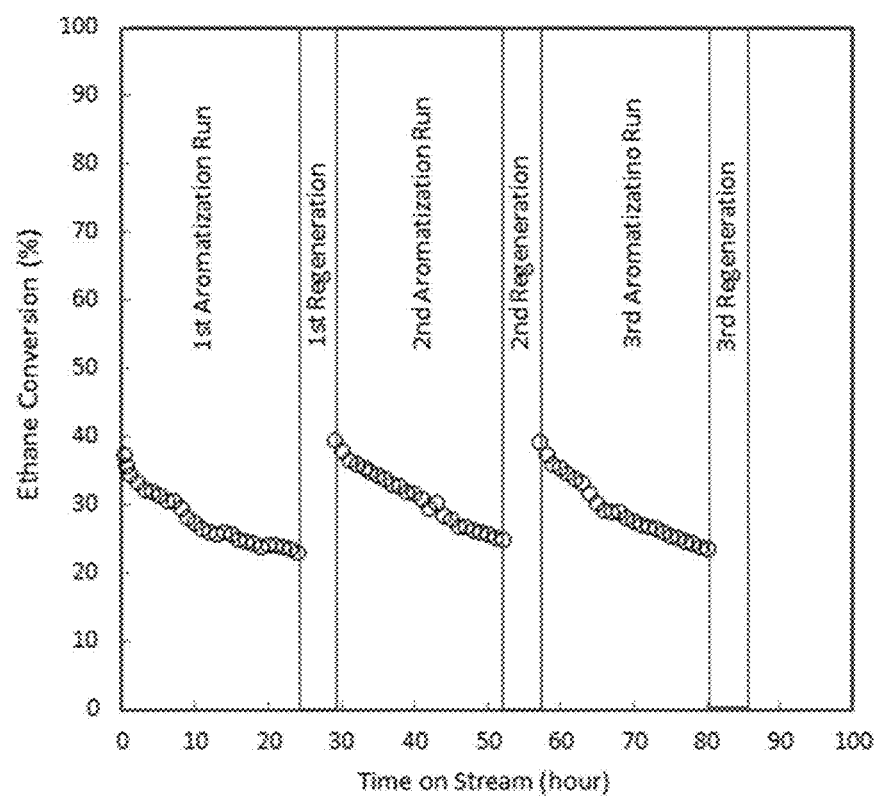
FIG. 7 shows ethane feed conversion after catalyst regeneration for Catalyst C (0.04 wt % Pt-1.6 wt % Ga/ZSM-5/Binder) in a fluidized bed reactor as described in Example 2.

FIG. 7 shows ethane conversion over the fresh catalyst for the first 24 hour period (or time on stream) and another two repeated 24 hour runs over regenerated catalyst. It is seen that the regeneration step practiced provides reproducible ethane conversion rate without noticeable degradation in the catalyst performance.

Table 2 summarizes performance data averaged over the run period for the three 24 hour period aromatics production runs as shown in FIG. 7.

TABLE 2

|  | 1st Run | 2nd Run | 3rd Run |
| --- | --- | --- | --- |
| Ethane Conversion | 27.3 | 31.1 | 29.5 |
| Selectivities, % (carbon basis) | | | |
| Methane | 11.8 | 13.6 | 13.6 |
| Ethylene | 10.4 | 7.5 | 8.1 |
| Propane | 5.3 | 5.8 | 6.0 |
| Propylene | 2.3 | 2.1 | 2.2 |
| Liquid (C6+) | 68.6 | 69.9 | 68.6 |
| Benzene | 15.2 | 16.7 | 15.7 |
| Toluene | 22.2 | 23.9 | 23.5 |
| Xylene | 6.3 | 6.7 | 6.6 |
| Ethylbenzene | 0.8 | 0.7 | 0.7 |
| Styrene | 0.2 | 0.1 | 0.1 |
| C9 Aromatic | 3.6 | 3.2 | 3.2 |
| Naphthalene | 7.8 | 7.5 | 7.7 |
| 2-Methylnaphthalene | 6.2 | 5.5 | 5.5 |
| 1-Methylnaphthalene | 2.4 | 2.0 | 2.0 |
| Other Aromatic Hydrocarbons | 4.0 | 3.6 | 3.5 |
| Coke | 1.6 | 1.2 | 1.3 |

REFERENCE NUMBERS

A summary of the reference numbers used in FIGS. 1-4 are displayed below based on the Figure where they first appear.

FIG. 1
1. Reactor feed stream
2. Reactor effluent stream
3. Fuel gas-air mixed stream
4. Heat exchanger effluent
100. Reactor
101. Upper vessel
102. Lower vessel
103. Catalytic combustor inlet
104. Heat exchanger outlet
105. Reactor inlet
106. Fluidization plate
107. Heat exchanger
108. Catalytic combustor
109. Flange connection
110. Bed of catalyst particles
111. Internal cyclone separators
112. Reactor outlet
113. Service port
FIG. 2
5. Reactor effluent stream
6. Reactor effluent stream
7. Liquid product
8. Gaseous product stream
9. Gaseous product stream after compressor
10. Light alkane recycle stream
11. Fuel gas stream
12. Combustion air
13. Light alkane recycle stream
14. Light alkane fresh feed
15. Reactor feed stream
16. Heat exchanger effluent stream
200. Single reactor process
201. Reactor sub-process
202. Heat exchanger
203. Heat exchanger
210. Separation sub-process
211. Heat exchanger
212. Vapor-liquid separator
213. Compressor
214. Demethanizer
FIG. 3
9a. Gas-liquid mixture
9b. Gas stream
9c. Liquid stream
9d. Liquid stream
9e. Liquid stream
9f. Overhead gas product stream
9g. Bottom product stream
301. Turboexpander
302. Cold box
303. Gas-liquid separator
304. Demethanizer fractionation column
305. Valve
306. Pump
FIG. 4
17. Diluted air
18. Catalyst regeneration effluent stream
220. Reactor sub-process
221. Reactor sub-process
222. Reactor sub-process
250. Multiple reactor sub-process
300. Multiple reactor process

I claim:

1. A process for producing aromatic hydrocarbons comprising:
   feeding a light alkane feedstock comprising at least 50% ethane by weight into a fluidized bed reactor, and
   contacting the feedstock with a catalyst bed at a temperature of less than 620° C. and a pressure between 0-200 psig to produce a reactor effluent stream comprising aromatic hydrocarbons,
   wherein the fluidized bed reactor comprises a catalyst bed, a heat exchanger embedded in the catalyst bed, and a catalytic combustor inside the heat exchanger,
   wherein the catalyst bed comprises a bi-functional catalyst, and
   wherein the bi-functional catalyst comprises a dehydrogenation catalyst and a solid acid catalyst.

2. The process of claim 1 further comprising:
   separating the reactor effluent stream into an aromatic hydrocarbons stream and a gaseous products stream;
   separating the gaseous products stream into a fuel gas stream containing hydrogen and methane and a hydrocarbon recycle stream containing C2, C3, C4, and C5 hydrocarbons;
   recycling the fuel gas stream for heat generation; and
   recycling the hydrocarbon recycle stream into the light alkane feedstock.

3. The process of claim 1, wherein the fluidized bed reactor is operated in either a bubbling fluidization or a turbulent fluidization regime.

4. The process of claim 1, wherein the fluidized bed reactor comprises single or a plurality of reactors arranged in parallel.

5. The process of claim 1, wherein the fluidized bed reactor comprises at least one reactor in an aromatic hydrocarbons production mode and at least one reactor in a catalyst regeneration mode.

6. The process of claim 1, wherein the fluidized bed reactor can undergo a transition between an aromatic hydrocarbon production mode and a catalyst regeneration mode for continuous production of aromatic hydrocarbons.

7. The process of claim 1, wherein the catalyst is regenerated by combustion of coke, wherein diluted air is provided for coke burn-off at about 400-600° C. reactor temperature and at 0-200 psig reactor pressure while fluidization of catalyst particles in bubbling or turbulent fluidization regime is maintained throughout the regeneration period.

8. The process of claim 1 wherein the aromatic hydrocarbon production mode operates between 12 hours and 96 hours before transitioning to catalyst regeneration mode.

9. The process of claim 1, wherein weight hourly space velocity (WHSV) of the said fluidized bed reactor in aromatic hydrocarbon production mode operation is about 0.5 to 5.0 per hour.

10. The process of claim 1, wherein said dehydrogenation catalyst is selected from the group consisting of platinum, rhodium, gallium, iron, indium, palladium, and nickel.

11. The process of claim 1, wherein said solid acid catalyst is zeolite selected from the group consisting of ZSM-5, ZSM-11, ZSM-12, ZSM-23, ZSM-35 and ZSM-48.

12. The process of claim 1, wherein said bi-functional catalyst comprises ZSM-5 loaded with 0.02-0.2 wt % platinum and 0.5-2.0 wt % gallium, metal basis.

13. The process of claim 1, wherein said bi-functional catalyst is particles of 30-300 micrometer in diameter.

14. The process of claim 1, wherein the bi-functional catalyst further comprises 10-50 wt % binder material selected from alumina, silica or clay.

15. The process of claim 1, wherein said temperature is 400-620° C., 500-600° C., 520-600° C., or 550-590° C.

16. The process of claim 1, wherein said pressure is 0-200 psig, 40-200 psig, or 60-200 psig.

17. A method for producing aromatic hydrocarbons comprising:
   operating a reaction process and a separation process, wherein
      the reaction process comprises feeding a light alkane feedstock comprising at least 50% ethane by weight into a plurality of fluidized bed reactors to produce a reactor effluent stream, wherein each fluidized bed reactor comprises an upper vessel, a lower vessel, a catalyst bed, a heat exchanger, catalytic combustor, fluidization plate and a plurality of internal cyclones, and
      the separation process comprises separating said reactor effluent stream into an aromatic hydrocarbon stream and a gaseous product stream using a heat exchanger and a vapor-liquid separator,
   operating one fluidized bed reactor in the reaction process in catalyst regeneration mode with diluted air while operating the remaining fluidized bed reactors in aromatic hydrocarbons production mode,
   separating said gaseous product stream into a fuel gas stream comprising methane and hydrogen and a hydrocarbon recycle stream comprising C2-C5 hydrocarbons using a compressor and a demethanizer,
   recycling said fuel gas stream to said catalytic combustor of said fluidized bed reactors, and
   recycling said hydrocarbon recycle stream to said light alkane feedstock; and
      wherein the individual fluidized bed reactors can be operated in production mode operation or regeneration mode operation for continuous and uninterrupted production of aromatic hydrocarbons.

* * * * *